(12) United States Patent
Miyamoto

(10) Patent No.: US 8,439,829 B2
(45) Date of Patent: May 14, 2013

(54) ENDOSCOPE, DISTAL END CAP-EQUIPPED ENDOSCOPE AND ENDOSCOPE CLEANING SHEATH

(75) Inventor: Shinichi Miyamoto, Hachioji (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 13/289,738

(22) Filed: Nov. 4, 2011

(65) Prior Publication Data

US 2012/0046524 A1 Feb. 23, 2012

Related U.S. Application Data

(62) Division of application No. 12/414,987, filed on Mar. 31, 2009, now abandoned.

(30) Foreign Application Priority Data

Apr. 4, 2008 (JP) ................................. 2008-098557

(51) Int. Cl.
*A61B 1/12* (2006.01)

(52) U.S. Cl.
USPC ........... 600/157; 600/121; 600/158; 600/169; 600/129

(58) Field of Classification Search ........... 600/101–183
See application file for complete search history.

(56) References Cited

U.S. PATENT DOCUMENTS

| 6,409,657 B1 | 6/2002 | Kawano |
| 2007/0260120 A1 | 11/2007 | Otawara |
| 2008/0188715 A1 | 8/2008 | Fujimoto |

FOREIGN PATENT DOCUMENTS

| JP | 6-014870 | 1/1994 |
| JP | 7-136102 | 5/1995 |
| JP | 10-151108 | 6/1998 |
| JP | 11-188004 | 7/1999 |

*Primary Examiner* — Matthew J Kasztejna
*Assistant Examiner* — Kevin G Barry, III
(74) *Attorney, Agent, or Firm* — Ostrolenk Faber LLP

(57) ABSTRACT

An endoscope includes, an insertion section, a distal end section body has an observation window, a liquid feed path which is formed to supply a liquid to the distal end section body side, a gas feed path which is formed to supply a gas to the distal end section body side, and a nozzle having a confluent portion which makes confluent the liquid supplied from the liquid feed path and the gas supplied from the gas feed path, and a jet outlet which jets a gas/liquid mixture fluid, which is mixed in the confluent portion, toward the observation window, wherein the nozzle is configured such that an angle, which is formed between a direction of a flow of the liquid toward the jet outlet and a direction of a flow of the gas toward the jet outlet, is set at an obtuse angle of 90° or more.

15 Claims, 9 Drawing Sheets

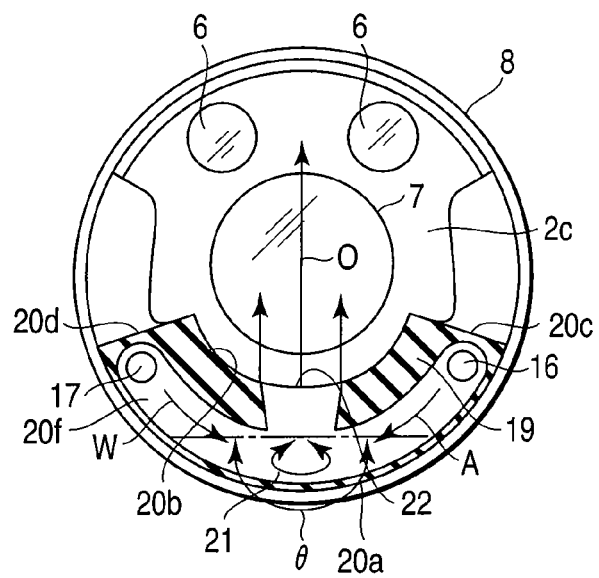
F I G. 5A
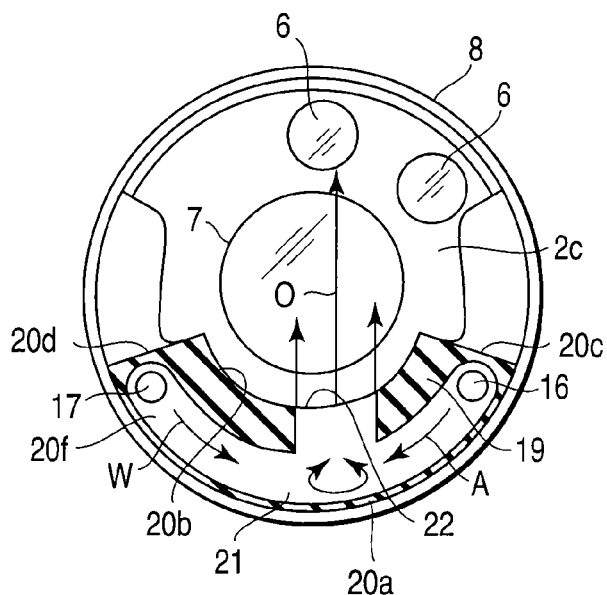
F I G. 5B

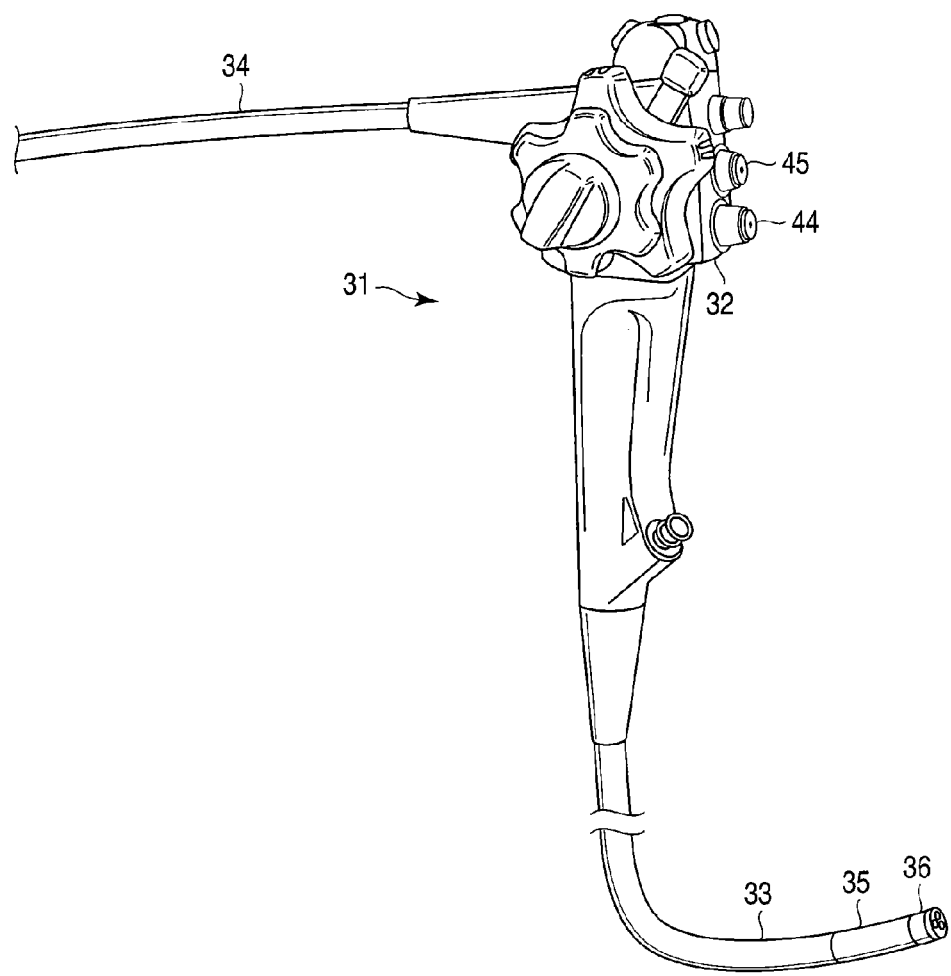
F I G. 6

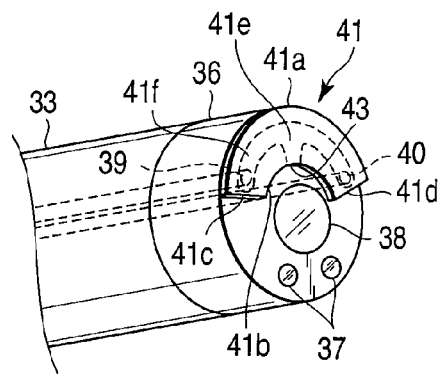
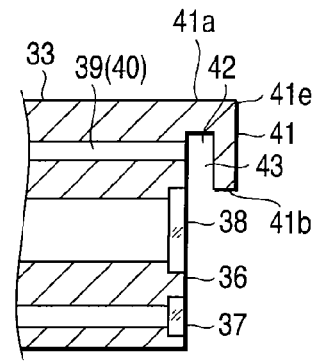
FIG. 7          FIG. 8
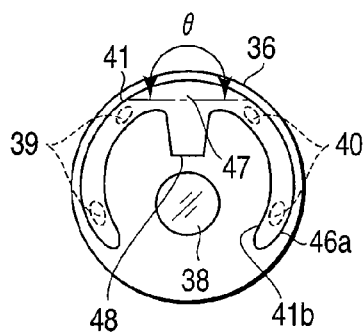
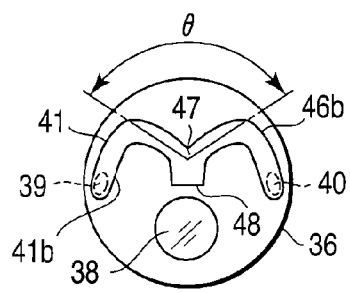
FIG. 9A          FIG. 9B
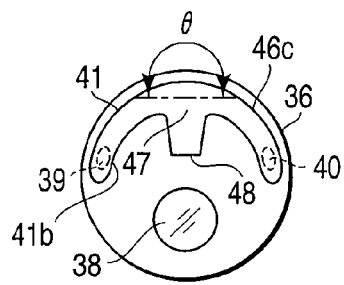
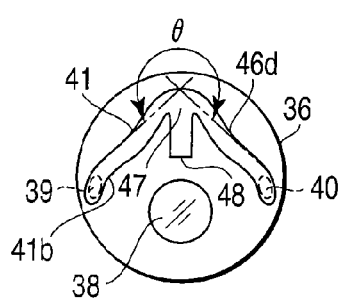
FIG. 9C          FIG. 9D

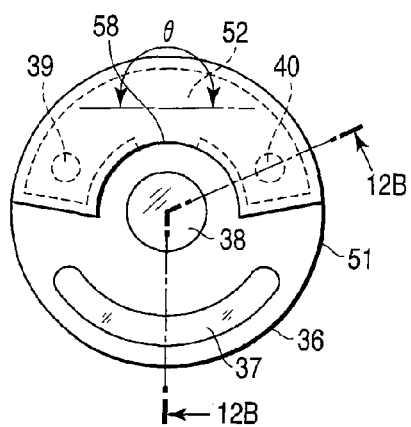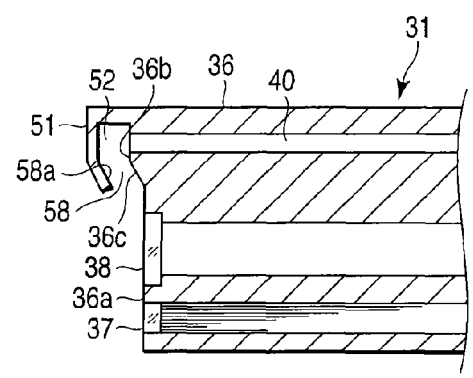
F I G. 12A  F I G. 12B
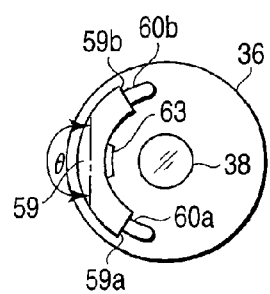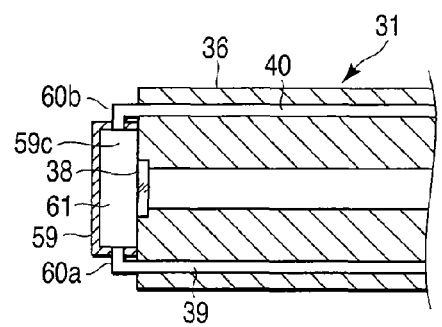
F I G. 13A  F I G. 13B

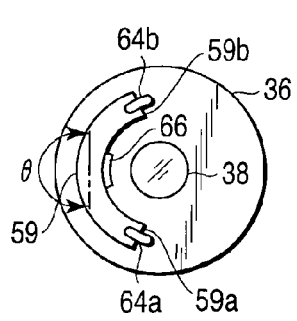
F I G. 14A
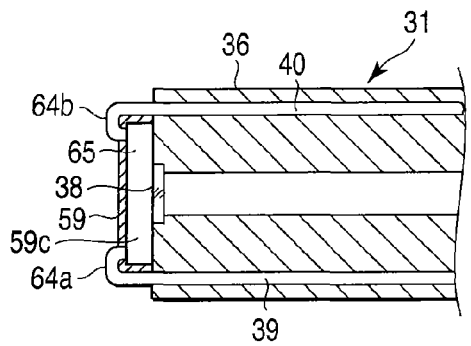
F I G. 14B
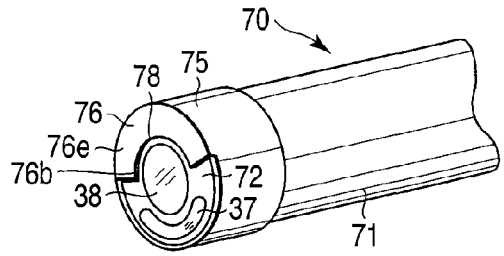
F I G. 15
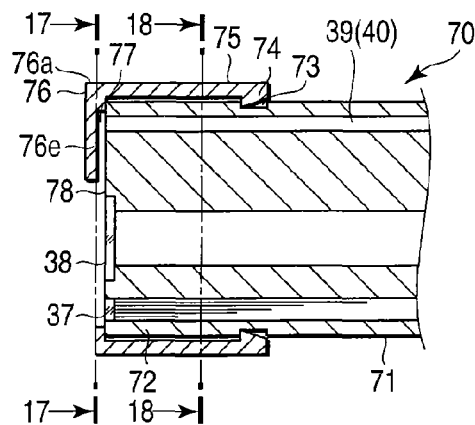
F I G. 16

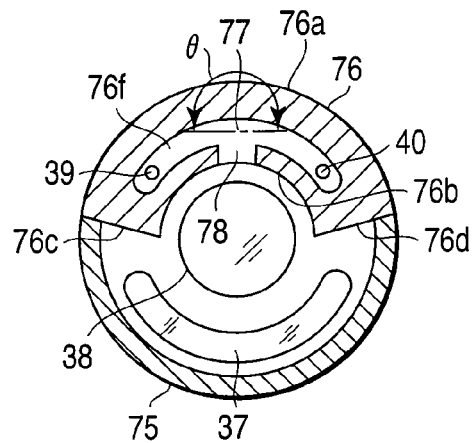
F I G. 17
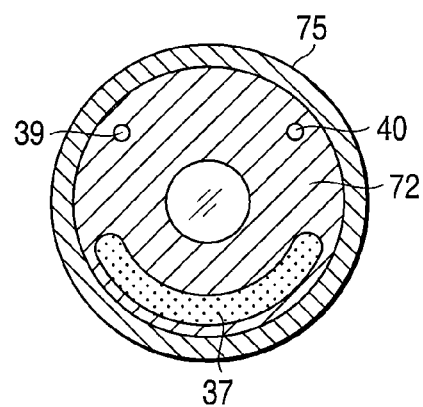
F I G. 18

ENDOSCOPE, DISTAL END CAP-EQUIPPED ENDOSCOPE AND ENDOSCOPE CLEANING SHEATH

CROSS-REFERENCE TO RELATED APPLICATIONS

This application is a divisional under 37 C.F.R. §1.53(b) of prior application Ser. No. 12/414,987 filed Mar. 31, 2009, entitled ENDOSCOPE, DISTAL END CAP-EQUIPPED ENDOSCOPE AND ENDOSCOPE CLEANING SHEATH in the name of Shinichi Miyamoto, which is based upon and claims the benefit of priority from prior Japanese Patent Application No. 2008-098557, filed Apr. 4, 2008, the entire contents of which are incorporated herein by reference.

BACKGROUND OF THE INVENTION

1. Field of the Invention

The present invention relates to an endoscope including a fluid jet nozzle for cleaning, e.g. contamination adhering to an observation window which is provided on a distal end section body of the endoscope, a distal end cap-equipped endoscope, and an endoscope cleaning sheath.

2. Description of the Related Art

In a medical endoscope, an insertion section, which is inserted into a body cavity, is provided with an illumination window and an observation window at a distal end section body thereof. While emitting illumination light from the illumination window and illuminating the body cavity, observation is performed through the observation window. The distal end section body is provided with a fluid jet nozzle. In a case where blood, mucus or the like adheres to the illumination window or observation window and the field of vision is deteriorated, water and air are jetted from the fluid jet nozzle, thereby to clean the illumination window or observation window.

Jpn. Pat. Appln. KOKAI Publication No. H11-188004 (patent document 1) discloses the following structure. A distal end cap is detachably attached to a distal end section body of an insertion section of an endoscope. This distal end cap includes the air/water feed nozzle as mentioned above.

An air feed path and a water feed path are formed in the distal end section body. Distal end portions of a water feed tube and an air feed tube are connected, respectively, to the air feed path and the water feed path. A communication path, at which the air feed path and the water feed path are made confluent, is provided in the distal end section body. The air/water feed nozzle is connected to the communication path.

Proximal end portions of the water feed tube and air feed tube are connected to water feed means and air feed means on the proximal side of the insertion section. Water and air are supplied to the water feed tube and air feed tube from the water feed means and air feed means on the proximal side of the insertion section. In this structure, the water, which is fed from the water feed tube, and the air, which is fed from the air feed tube, are supplied to the air/water feed nozzle via the communication path in the distal end section body, and the water and air are jetted from the air/water feed nozzle to the observation window.

Jpn. Pat. Appln. KOKAI Publication No. H10-151108 (patent document 2), like patent document 1, discloses a structure wherein a water feed tube and an air feed tube are connected to a water feed path and an air feed path in a distal end section body of an endoscope, and the water feed tube and the air feed tube are made confluent in a communication path which is provided in the distal end section body. In addition, an air/water feed nozzle having a distal end portion with a reduced diameter is connected to the communication path. In this structure, water and air are jetted from the air/water feed nozzle to the observation window.

Jpn. Pat. Appln. KOKAI Publication No. H7-136102 (patent document 3) discloses the following structure. An air feed outlet and a water feed outlet, which open at a distal end face of a distal end potion body of an insertion section of an endoscope, are provided adjacent to each other. In the distal end section body, a nozzle is detachably attached in such a manner that the nozzle is opposed to the air feed outlet and water feed outlet. In this structure, the direction of jet of the air, which is fed from the air feed outlet, and the direction of jet of the water, which is fed from the water feed outlet, are varied by the nozzle, and the air and water are jetted toward the observation window.

Jpn. Pat. Appln. KOKAI Publication No. H6-14870 (patent document 4) discloses the following structure. An air feed path and a water feed path are provided in an insertion section of an endoscope. The air feed path and water feed path are made confluent in the insertion section, and made to communicate with an air/water feed nozzle. Further, air is intermittently blown into the water flowing in the water feed path, thus producing an air/water mixture fluid and enhancing the performance of cleaning.

BRIEF SUMMARY OF THE INVENTION

According to a first aspect of the present invention, an endoscope comprising: an insertion section which is inserted in a body cavity; a distal end section body which constitutes a distal end section of the insertion section and has at least an observation window; a liquid feed path which is formed to supply a liquid to the distal end section body side and communicates with a liquid feed source; a gas feed path which is formed to supply a gas to the distal end section body side and communicates with a gas feed source; and a nozzle having a confluent portion which makes confluent the liquid supplied from the liquid feed path and the gas supplied from the gas feed path, and a jet outlet which jets a gas/liquid mixture fluid, which is mixed in the confluent portion, toward the observation window, wherein the nozzle is configured such that an angle, which is formed between a direction of a flow of the liquid toward the jet outlet and a direction of a flow of the gas toward the jet outlet, is set at an obtuse angle of more than 90°.

According to another aspect of the present invention, a distal end cap-equipped endoscope comprising: an insertion section which is inserted in a body cavity; a distal end section body which constitutes a distal end section of the insertion section and has at least an observation window; a liquid feed path which is formed to supply a liquid to the distal end section body side and communicates with a liquid feed source; a gas feed path which is formed to supply a gas to the distal end section body side and communicates with a gas feed source; a distal end cap which is detachably attached to the distal end section body; and a nozzle which is provided in the distal end cap and has a confluent portion which makes confluent the liquid supplied from the liquid feed path and the gas supplied from the gas feed path, and a jet outlet which jets a gas/liquid mixture fluid, which is mixed in the confluent portion, toward the observation window, wherein the nozzle is configured such that an angle, which is formed between a direction of a flow of the liquid toward the jet outlet and a direction of a flow of the gas toward the jet outlet, is set at an obtuse angle of more than 90°.

According to another aspect of the present invention, an endoscope cleaning sheath comprising: a cleaning sheath body which is fitted over an insertion section of an endoscope having at least an observation window at a distal end section body; a liquid feed path which is provided in the cleaning sheath body and communicates with a liquid feed source; a gas feed path which is provided in the cleaning sheath body and communicates with a gas feed source; and a nozzle which is provided in the cleaning sheath body and has a confluent portion which makes confluent the liquid supplied from the liquid feed path and the gas supplied from the gas feed path, and a jet outlet which jets a gas/liquid mixture fluid, which is mixed in the confluent portion, toward the observation window, wherein the nozzle is configured such that an angle, which is formed between a direction of a flow of the liquid toward the jet outlet and a direction of a flow of the gas toward the jet outlet, is set at an obtuse angle of more than 90°.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5A is a cross-sectional view taken along line 5A-5A in FIG. 3;

FIG. 5B is a cross-sectional view showing a modification of the structure of FIG. 5A;

FIG. 6 is a perspective view of a flexible endoscope according to a second embodiment of the present invention;

FIG. 7 is a perspective view of a distal end section of the endoscope according to the second embodiment;

FIG. 8 is a longitudinal cross-sectional side view of the distal end section of the endoscope according to the second embodiment;

FIG. 9A is a schematic front view showing a first modification of a nozzle of the second embodiment;

FIG. 9B is a schematic front view showing a second modification of the nozzle of the second embodiment;

FIG. 9C is a schematic front view showing a third modification of the nozzle of the second embodiment;

FIG. 9D is a schematic front view showing a fourth modification of the nozzle of the second embodiment;

FIG. 12A is a front view of a distal end section body according to a fourth embodiment of the present invention;

FIG. 12B is a cross-sectional view taken along line 12B-12B in FIG. 12A;

FIG. 13A is a front view of a distal end section body according to a fifth embodiment of the present invention;

FIG. 13B is a longitudinal cross-sectional side view of the distal end section body in the fifth embodiment;

FIG. 14A is a front view of a distal end section body according to a sixth embodiment of the present invention;

FIG. 14B is a longitudinal cross-sectional side view of the distal end section body in the sixth embodiment;

FIG. 15 is a perspective view of a distal end cap-equipped endoscope according to a seventh embodiment of the invention;

FIG. 16 is a longitudinal cross-sectional side view of a distal end section body of the distal end cap-equipped endoscope according to the seventh embodiment;

FIG. 17 shows the seventh embodiment and is a cross-sectional view taken along line 17-17 in FIG. 16; and FIG. 18 shows the eleventh embodiment and is a cross-sectional view taken along line 18-18 in FIG. 16.

DETAILED DESCRIPTION OF THE INVENTION

Figure 1:
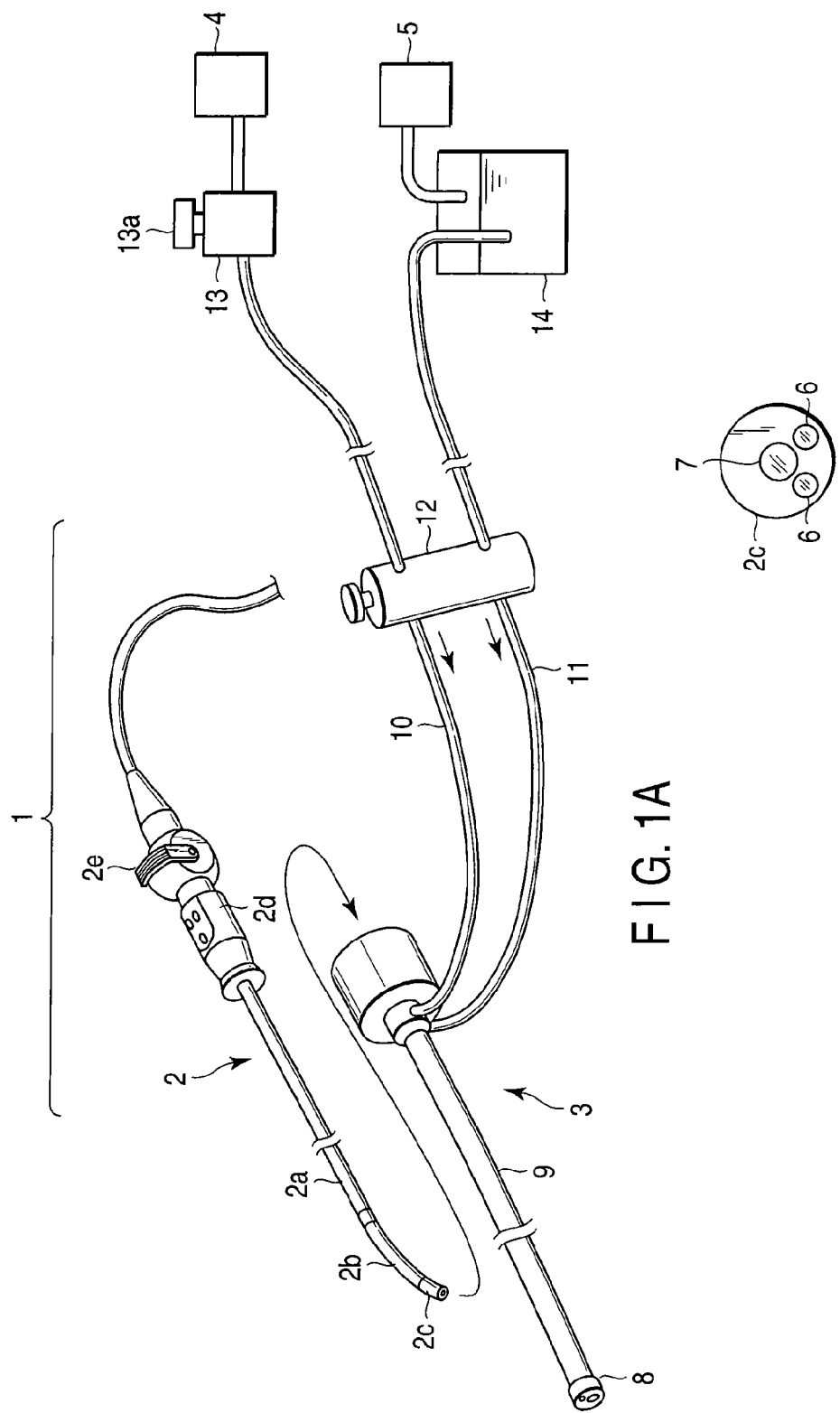
FIG. 1A is a perspective view showing the entire structure of an endoscope and an endoscope cleaning sheath according to a first embodiment of the present invention.
FIG. 1B is a front view of a distal end section body of the endoscope of the first embodiment.

Embodiments of the present invention will now be described with reference to the accompanying drawings. FIG. 1A to FIG. 5A show a first embodiment of the present invention. FIG. 1A is a perspective view showing the entire structure of an endoscope apparatus 1, and FIG. 1B is a front view of a distal end section body 2c of an endoscope 2.

As shown in FIG. 1A, the endoscope apparatus 1 comprises the endoscope 2, an endoscope cleaning sheath 3, a gas feed pump 4 functioning as a gas feed device, and a liquid feed pump 5 functioning as a liquid feed device. The endoscope 2 is, for example, a rigid endoscope having a bending section 2b in an insertion section 2a thereof. A distal end portion of the insertion section 2a is provided with a distal end section body 2c. A proximal end portion of the insertion section 2a is provided with an operation section 2d. The operation section 2d is provided with a bending operation lever 2e for bending the bending section 2b in an up-and-down direction or in a right-and-left direction.

The endoscope cleaning sheath 3 is fitted over the insertion section 2a of the endoscope 2. Thereby, the endoscope cleaning sheath 3, as one piece with the insertion section 2a, is inserted into a body cavity. As shown in FIG. 1B, a distal end face of the distal end section body 2c is provided with two illumination windows 6 and one observation window 7. The illumination widows 6 constitute parts of an illumination optical system. The observation window 7 constitutes a part of an observation optical system.

The illumination window 6 is connected to a light source device (not shown) via a light guide fiber. The observation optical system is provided with an image pickup device including an image pickup element, such as a CCD, which photoelectrically converts an optical image, which is captured through the observation window 7, to an electric signal. A signal cable extends from the image pickup device. This signal cable is connected to an external camera control unit (not shown). Thus, reflective light from a subject, which is illuminated with illumination light that is emitted from the illumination window 6, is received as an optical image via the observation window 7. The optical image, after converted to the electric signal by the image pickup element, is transmitted to the camera control unit. The camera control unit generates a video signal on the basis of the electric signal, and outputs the video signal to, for example, a liquid crystal display which is a display device, thus displaying an endoscopic image on the screen of the liquid crystal display.

The endoscope cleaning sheath 3 is formed as an elongated cylindrical member. The insertion section 2a of the endoscope 2 is detachably inserted into the endoscope cleaning sheath 3. Thereby, the endoscope cleaning sheath 3 is disposed in a manner to cover the entirety of the insertion section 2a of the endoscope 2.

The endoscope cleaning sheath 3 is mainly composed of a distal end cover 8 which is a cylindrical body, and a tube body 9 which is composed of a multi-lumen tube. The distal end cover 8 is fitted on a distal end portion of the tube body 9. The proximal end side of the tube body 9 is provided with an operation section coupling unit 81 which has a greater diameter than the tube body 9. One end of a gas supply tube 10 and one end of a liquid supply tube 11 are coupled to the operation section coupling unit 81. The distal end cover 8 and the tube body 9 may be integrally formed, or may be formed of the same material.

The other end of the gas supply tube 10 is connected to the gas feed pump (gas feed source) 4 via an opening/closing valve 12 and a pressure adjusting valve 13, which are provided at positions along the gas supply tube 10. The other end of the liquid supply tube 11 is connected to the liquid feed pump (liquid feed source) 5 via the opening/closing valve 12 and a liquid feed tank 14, which are provided at positions along the liquid supply tube 11.

The tube body 9, which is composed of the multi-lumen tube, is formed of a flexible material such as silicone, urethane or TEFLON (Dupont trademark for polytetrafluoroethylene), or a rigid material such as polyamide, polyethylene, polypropylene or polycarbonate.

Figure 2:
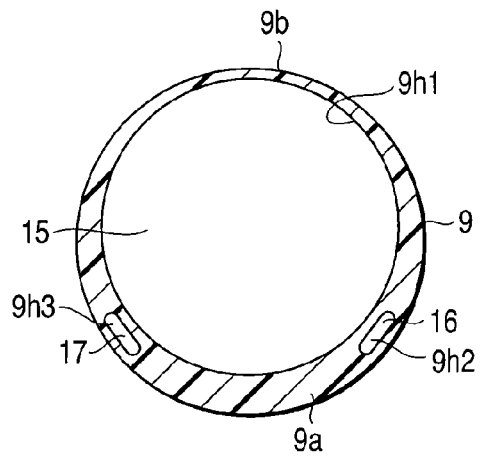
FIG. 2 is a transverse cross-sectional view of a sheath body in the first embodiment.

As shown in FIG. 2, the tube body 9 has an eccentric hole 9h1, the center axis of which is eccentric to the outer peripheral surface of the tube body 9. Thereby, the peripheral wall of the tube body 9, which defines the eccentric hole 9h1, includes a large thickness portion 9a and a small thickness portion 9b. The eccentric hole 9h1 of the tube body 9 is a through-hole having openings at a distal end face and a proximal end face of the tube body 9. The eccentric hole 9h1 is used as an endoscope hole 15 in which the insertion section 2a of the endoscope 2 is inserted.

The large thickness portion 9a of the tube body 9 includes two through-holes 9h2 and 9h3, which penetrate the large thickness portion 9a in the axial direction of the tube body 9. One through-hole 9h2 is used as a gas feed path 16 serving as a first flow path for supplying a gas such as air. The other through-hole 9h3 is used as a liquid feed path 17 serving as a second flow path for supplying a liquid such as water or a cleaning solution. The proximal end side of the gas feed path 16 communicates with the gas supply tube 10, and the proximal end side of the liquid feed path 17 communicates with the liquid supply tube 11.

Figure 4:
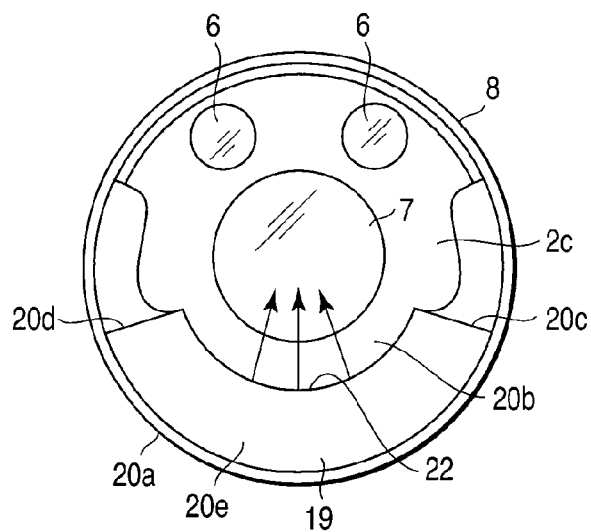
FIG. 4 is a front view showing the distal end section of the endoscope in the first embodiment.

As shown in FIG. 4, the distal end cover 8 of the endoscope cleaning sheath 3 is a circular cylindrical member. The distal end cover 8 is provided with an opening portion 18 at a part thereof that is opposed to the front surface of the distal end section body 2c of the endoscope 2.

A nozzle 19, which is bent inward in a substantially L shape, is integrally provided in a front end portion of the distal end cover 8. As shown in FIG. 5A, the nozzle 19 has a space portion 20f which is surrounded by an outer peripheral wall 20a extending along the outer peripheral portion of the distal end section body 2c, an inner peripheral wall 20b surrounding a part of the outer periphery of the observation window 7, a right side wall 20c which defines a right side surface of the nozzle 19 in FIG. 5A, a left side wall 20d which defines a left side surface of the nozzle 19, and an arcuate front wall 20e (see FIG. 4).

Figure 3:
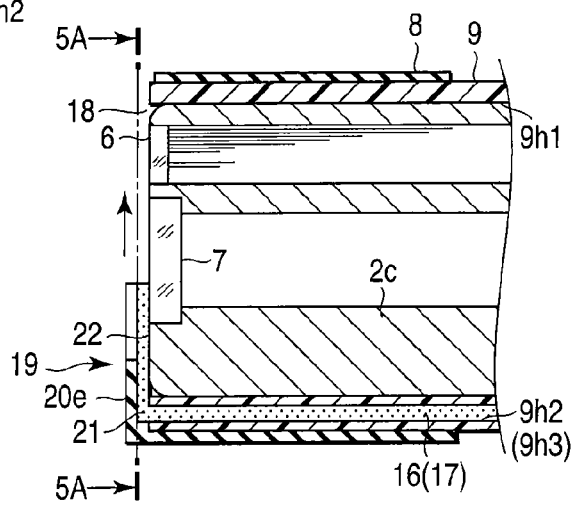
FIG. 3 is a longitudinal cross-sectional side view of the distal end section of the endoscope in the first embodiment.

Further, the gas feed path 16 is open on the right wall 20c side in the space portion 20f of the nozzle 19. On the left wall 20d side, the liquid feed path 17 is open. Accordingly, as shown in FIG. 3, the gas feed path 16 and the liquid feed path 17 open toward the front end side of the distal end section body 2c of the endoscope 2, and are opposed to the inner surface of the front wall 20e of the nozzle 19.

A confluent portion 21 is provided in an intermediate part in the longitudinal direction of the nozzle 19. The flow of the gas (arrow A in FIG. 5A), which is supplied from the gas feed path 16 and flows in the space portion 20f of the nozzle 19, and the flow of the liquid (arrow W in FIG. 5A), which is supplied from the liquid feed path 17 and flows in the space portion 20f of the nozzle 19, are made confluent in the confluent portion 21. At this time, the angle θ, which is formed between the direction of the flow A of the gas, which is supplied from the gas feed path 16, and the direction of the flow W of the liquid, which is supplied from the liquid feed path 17, is set at an obtuse angle of more than 90°, for example, at an obtuse angle of about 180°, as shown in FIG. 5A. Specifically, the angle θ is set at such an angle that when the gas (arrow A) supplied from the gas feed path 16 and the liquid (arrow W) supplied from the liquid feed path 17 collide in the confluent portion 21, the gas and the liquid are easily mixed and made turbulent. Thereby, when the flow A of the gas supplied from the gas feed path 16 and the flow W of the liquid supplied from the liquid feed path 17 flow within the space portion 20f of the nozzle 19 and are made confluent in the confluent portion 21, the gas and the liquid are caused to temporarily stay there, and are mixed.

The diameter of the flow path of the confluent portion 21 is set to be greater than the diameter of the flow path of each of the gas feed path 16 and liquid feed path 17. Thereby, the gas and the liquid collide with each other and are made turbulent in the confluent portion 21, and the gas and liquid are efficiently mixed.

A jet outlet 22 is provided in the inner peripheral wall 20b of the nozzle 19, which is opposed to the confluent portion 21. The jet outlet 22 is formed of a rectangular elongated hole that is elongated in the longitudinal direction of the nozzle 19. Thereby, the gas/liquid mixture fluid, which is made confluent and mixed in the confluent portion 21, is jetted toward the observation window 7 and illumination windows 6 from the jet outlet 22.

The confluent portion 21 of the nozzle 19 having the above-described structure is provided on the plane that continuously extends to the observation window 7 of the distal end section body 2c. Thus, the gas (arrow A) that is supplied from the gas feed path 16 and the liquid (W) that is supplied from the liquid feed path 17 are mixed in the confluent portion 21, and an atomized gas/liquid mixture fluid is produced. This atomized gas/liquid mixture fluid is jetted toward the observation window 7 from the jet outlet 22. Thereby, contamination (mucus, blood, etc.) adhering to the observation window 7 is blown off and cleaned by the atomized gas/liquid mixture fluid that is jetted from the jet outlet 22. In the present embodiment, since the illumination windows 6 are also disposed on the continuous plane, contamination adhering to the illumination windows 6 can be blown off and cleaned at the same time by the atomized gas/liquid mixture fluid that is jetted from the jet outlet 22.

Next, the operation of the first embodiment is described. When the endoscope 1 is used, the endoscope cleaning sheath 3 is set in advance in the state in which the endoscope cleaning sheath 3 is fitted over the insertion section 2a of the endoscope 2. At this time, the entirety of the insertion section 2a is covered with the tube body 9. The distal end section body 2c of the endoscope 2 is covered with the distal end cover 8. The jet outlet 22 of the nozzle 19 of the distal end cover 8 is disposed to be directed to the observation window 7 and illumination windows 6 of the distal end section body 2c.

In the state in which the endoscope cleaning sheath 3 is fitted over the endoscope 2, the insertion section 2a of the endoscope 2, as one piece with the endoscope cleaning sheath 3, is inserted into a body cavity of a patient. The inside of the body cavity is observed by the endoscope 2, and a diseased part is treated, where necessary. At this time, there is a case in which contamination adheres to the observation window 7 and the field of vision is deteriorated. In this case, the observation window 7 can be cleaned remotely by the operation, which will be described below.

Specifically, at the time of the work of cleaning the observation window 7, the gas feed pump 4 is driven to feed gas and simultaneously the liquid feed pump 5 is driven to feed liquid. If the gas is fed from the gas feed pump 4, the gas is supplied to the gas feed path 16 via the gas supply tube 10. If the liquid is fed from the liquid feed pump 5, the liquid is supplied to the liquid feed path 17 via the liquid supply tube 11. Further, the gas in the gas feed path 16 and the liquid in the liquid feed path 17 are supplied into the space portion 20f of the nozzle 19. At this time, the flow A of the gas supplied from the gas feed path 16 and the flow W of the liquid supplied from the liquid feed path 17 collide at an obtuse angle and are made turbulent in the confluent portion 21, and the liquid and gas are mixed into an atomized gas/liquid mixture fluid. The atomized gas/liquid mixture fluid is jetted from the jet outlet 22 toward the observation window 7.

Since the confluent portion 21 of the nozzle 19 is provided on the plane that is continuous with the observation window 7 of the distal end section body 2c, the atomized gas/liquid mixture fluid, which is mixed in the confluent portion 21, can be jetted from the jet outlet 22 toward the observation window 7. As a result, the contamination adhering to the observation window 7 can efficiently be blown off and cleaned by the atomized gas/liquid mixture fluid that is jetted from the jet outlet 22 toward the observation window 7. Moreover, since the gas/liquid mixture fluid is the atomized fluid, particles of water are fine and immediately evaporate. Thus, no drops of water remain on the surface of the observation window 7. Therefore, the field of vision can instantaneously be secured.

In the case where the force of the atomized gas/liquid mixture fluid, which is jetted from the jet outlet 22, is to be increased, an adjustment knob 13a of the pressure adjusting valve 13 is controlled to increase the pressure of the gas. By this operation, the pressure of the gas that is supplied from the gas feed path 16 can be increased, and the gas/liquid mixture ratio can arbitrarily be controlled. In this case, in consideration of the difference in specific gravity between the gas and the liquid, the pressures of the gas feed pump 4 and liquid feed pump 5 may be preset to meet the relationship, i.e. the pressure of the gas feed pump 4>the pressure of the liquid feed pump 5.

FIG. 5B shows a modification of the structure of FIG. 5A. In the first embodiment, as shown in FIG. 5A, the two illumination windows 6 are disposed to be symmetric in the right and left direction with respect to the center position of the observation window 7. Accordingly, the axis O of the mixture fluid, which is jetted from the jet outlet 22 of the nozzle 19, extends to the center of the observation window 7. On the other hand, in the present modification, as shown in FIG. 5B, the two illumination windows 6 are disposed at eccentric positions with eccentricity to the right side in FIG. 5B from the center position of the observation window 7. In the case of this positional relationship, the position of the nozzle 19 is varied, with the axis O of the mixture fluid that is jetted from the jet outlet 22 being displaced from the center of the observation window 7. Thereby, both the observation window 7 and illumination windows 6 can effectively be cleaned.

The above-described first embodiment is directed to the case in which the cleaning tube is fitted over the rigid endoscope. Needless to say, however, the invention is applicable to the case in which the cleaning tube is fitted over a flexible endoscope.

FIG. 6 to FIG. 8 show a second embodiment of the present invention. In this embodiment, a flexible endoscope is integrally equipped with a cleaning function. FIG. 6 is a perspective view showing the entirety of the flexible endoscope.

As shown in FIG. 6, in a flexible endoscope 31, a flexible insertion section 33 and a universal cord 34 are coupled to an operation section 32. A distal end section body 36 is provided on the insertion section 33 via a bending section 35. As shown in FIG. 7, the distal end section body 36 is provided with two illumination windows 37 and one observation window 38. The two illumination windows 37 constitute parts of an illumination optical system. The observation window 38 constitutes a part of an observation optical system.

The illumination window 37 is connected to an external light source device (not shown) via a light guide fiber. The observation optical system is provided with an image pickup device including an image pickup element, such as a CCD, which photoelectrically converts an optical image, which is captured through the observation window 38, to an electric signal.

As shown in FIG. 8, the insertion section 33 is provided with a gas feed path 39 for supplying a gas such as air, and a liquid feed path 40 for supplying a liquid such as water or a cleaning solution. Like the first embodiment, the gas feed path 39 and liquid feed path 40 communicate with the gas feed pump 4 and liquid feed pump 5 through the insertion section 33, operation section 32 and universal cord 34.

An arcuate nozzle 41 is integrally provided at a front end portion of the distal end section body 36 of the endoscope 31 along the outer peripheral part of this front end portion. Specifically, the nozzle 41 has a space portion 41f which is surrounded by an outer peripheral wall 41a extending along the outer peripheral portion of the distal end section body 36, an inner peripheral wall 41b surrounding a part of the outer periphery of the observation window 38, a left end wall 41c which defines a left side surface of the nozzle 41 in FIG. 7, a right end wall 41d which defines a right side surface of the nozzle 41, and an arcuate front wall 41e. The space portion 41f is curved in an arcuate shape according to the curvature of the outer peripheral wall 41a and inner peripheral wall 41b. A taper portion, which is tapered toward the jet outlet 43 at the distal end opening, is formed at the intermediate part of the space portion 41f. Thereby, the space portion 41f of the nozzle 41 is formed in a substantially T-shape, as viewed in the frontal direction.

Further, the gas feed path 39 is open on the left end wall 41c side in the space portion 41f of the nozzle 41. On the right end wall 41d side, the liquid feed path 40 is open. Accordingly, the gas feed path 39 and the liquid feed path 40 are open to the front end side of the distal end section body 36, and are opposed to the inner surface of the front wall 41e of the nozzle 41.

An intermediate part in the longitudinal direction of the nozzle 41 is provided with a confluent portion 42 which combines and mixes the gas that is supplied from the gas feed path 39 and the liquid that is supplied from the liquid feed path 40. The flow of the gas supplied from the gas feed path 39 and the flow of the liquid supplied from the liquid feed path 40 collide at an obtuse angle and are made turbulent in the confluent portion 42, and the liquid and gas are mixed into an atomized gas/liquid mixture fluid.

Further, the inner peripheral wall 41b of the nozzle 41, which is opposed to the confluent portion 42, is provided with a jet outlet 43 of the nozzle 41. The jet outlet 43 is configured to jet the gas/liquid mixture fluid, which is made confluent and mixed in the confluent portion 42, toward the observation window 38 and illumination windows 37.

The confluent portion 42 of the nozzle 41 is provided on the plane that is continuous with the observation window 38 provided on the distal end section body 36. The gas supplied from the gas feed path 39 and the liquid supplied from the liquid feed path 40 collide in the confluent portion 42, and are made turbulent and mixed into an atomized gas/liquid mixture fluid. The atomized gas/liquid mixture fluid is jetted from the jet outlet 43 toward the observation window 38. Thus, contamination adhering to the observation window 38 can be blown off and cleaned.

Further, the operation section 32 is provided with a gas/liquid feed button 44 and a suction button 45. The gas/liquid feed button 44 controls the flow amount of the gas supplied from the gas feed path 39 and the flow amount of the liquid supplied from liquid feed path 40, and controls the gas/liquid mixture fluid that is jetted in an atomized state from the jet outlet 43 of the nozzle 41.

Like the first embodiment, the nozzle 41, observation window 38 and illumination windows 37 may successively be arranged so that the observation window 38 and illumination windows 37 may be cleaned by means of the nozzle 41.

Next, the operation of the second embodiment is described. In the present embodiment, the nozzle 41 is integrally provided on the distal end section body 36 of the insertion section 33 of the endoscope 31. In addition, the jet outlet 43 of the nozzle 41 is opposed to side portions of the observation window 38 and illumination windows 37. The insertion section 33 of the endoscope 31 is inserted into a body cavity of a patient, and the inside of the body cavity is observed and a diseased part is treated, where necessary. During this work, if contamination adheres to the observation window 38 and the field of vision is deteriorated, the observation window 38 can be cleaned remotely by the operation described below.

Specifically, the gas feed pump 4 is driven to feed gas and simultaneously the liquid feed pump 5 is driven to feed liquid. If the gas is fed from the gas feed pump 4, the gas is supplied to the gas feed path 39. If the liquid is fed from the liquid feed pump 5, the liquid is supplied to the liquid feed path 40. Further, the gas in the gas feed path 39 and the liquid in the liquid feed path 40 are supplied into the space portion 41f of the nozzle 41. The gas supplied from the gas feed path 39 flows from the opening end of the gas feed path 39 toward the confluent portion 42 within the space portion 41f. The liquid supplied from the liquid feed path 40 flows from the opening end of the liquid feed path 40 toward the confluent portion 42 within the space portion 41f. Thus, the gas supplied from the gas feed path 39 and the liquid supplied from the liquid feed path 40 collide in the confluent portion 42, and are made turbulent and mixed into an atomized gas/liquid mixture fluid. The atomized gas/liquid mixture fluid is jetted from the jet outlet 43 toward the observation window 38

At this time, the confluent portion 42 of the nozzle 41 is provided on the plane that is continuous with the observation window 38 of the distal end section body 36. Thus, the atomized gas/liquid mixture fluid, which is mixed in the confluent portion 42, is jetted from the jet outlet 43 toward the observation window 38, and the contamination adhering to the observation window 38 can efficiently be blown off and cleaned. Moreover, since the gas/liquid mixture fluid is the atomized fluid, no drops of water remain on the surface of the observation window 38, and the field of vision can instantaneously be secured.

In the case where the force of the atomized gas/liquid mixture fluid, which is jetted from the jet outlet 43, is to be increased, the gas/liquid feed button 44 that is provided on the operation section 32 is controlled to increase the pressure of the gas. Thereby, the pressure of the gas that is supplied from the gas feed path 39 can be increased, and the gas/liquid mixture ratio can arbitrarily be controlled.

FIG. 9A to FIG. 9D show different modifications of the nozzle 41 in the second embodiment. Each of FIG. 9A to FIG. 9D is a schematic front view of the distal end section body 36.

FIG. 9A shows a first modification of the nozzle 41 of the second embodiment. The nozzle 41 shown in FIG. 9A is provided with an arcuate portion 46a having a curvature according to the outer peripheral part of the distal end section body 36. A confluent portion 47 is provided at an intermediate part of the arcuate portion 46a. Further, a jet outlet 48, which opens toward a side part of the observation window 38 from the confluent portion 47, is provided in an inner peripheral wall 41b of the arcuate portion 46a. In addition, two gas feed paths 39 are open on the left side and two liquid feed paths 40 are open on the right side in such a manner that the two gas feed paths 39 and the two liquid feed paths 40 are symmetric with respect to the confluent portion 47 as a boundary. Besides, the angle θ, which is formed between the direction of the flow of the gas, which is supplied from the gas feed paths 39 toward the jet outlet 48, and the direction of the flow of the liquid, which is supplied from the liquid feed paths 40 toward the jet outlet 48, is set at an obtuse angle. Thus, the angle θ is set at such an angle that the gas and the liquid are easily mixed and made turbulent.

FIG. 9B shows a second modification of the nozzle 41 of the second embodiment. The nozzle 41 shown in FIG. 9B is provided with a substantially M-shaped conduit 46b with an obtuse angle along the outer peripheral part of the distal end section body 36. A confluent portion 47 is provided at an intermediate part of the conduit 46b. Further, a jet outlet 48, which opens toward a side part of the observation window 38 from the confluent portion 47, is provided in an inner peripheral wall 41b of the conduit 46b. In addition, one gas feed path 39 is open at the left end portion of the conduit 46b and one liquid feed path 40 is open at the right end portion. Besides, the angle θ, which is formed between the direction of the flow of the gas, which is supplied from the gas feed path 39, and the direction of the flow of the liquid, which is supplied from the liquid feed path 40, is set at an obtuse angle of more than 90°. Thus, the angle θ is set at such an angle that the gas and the liquid are easily mixed and made turbulent.

FIG. 9C shows a third modification of the nozzle 41 of the second embodiment. The nozzle 41 shown in FIG. 9C is provided with an arcuate conduit 46c having a curvature according to the outer peripheral part of the distal end section body 36. A confluent portion 47 is provided at an intermediate part of the conduit 46c. Further, a jet outlet 48, which opens toward a side part of the observation window 38 from the confluent portion 47, is provided in an inner peripheral wall 41b of the conduit 46c. In addition, a gas feed path 39 is open at the left end portion of the conduit 46c and a liquid feed path 40 is open at the right end portion. Besides, the angle θ, which is formed between the direction of the flow of the gas, which is supplied from the gas feed path 39, and the direction of the flow of the liquid, which is supplied from the liquid feed path 40, is set at an obtuse angle. Thus, the angle θ is set at such an angle that the gas and the liquid are easily mixed and made turbulent.

FIG. 9D shows a fourth modification of the nozzle 41 of the second embodiment. The nozzle 41 shown in FIG. 9D is provided with a substantially L-shaped conduit 46d in the distal end section body 36. A confluent portion 47 is provided at an intermediate part of the conduit 46d. Further, a jet outlet 48, which opens toward a side part of the observation window 38 from the confluent portion 47, is provided in an inner peripheral wall 41b of the conduit 46d. In addition, a gas feed path 39 is open at the left end portion of the conduit 46d and a liquid feed path 40 is open at the right end portion. Besides, the angle θ, which is formed between the direction of the flow of the gas, which is supplied from the gas feed path 39, and the direction of the flow of the liquid, which is supplied from the liquid feed path 40, is set at an obtuse angle. Thus, the angle θ is set at such an angle that the gas and the liquid are easily mixed and made turbulent.

According to each of the above-described modifications, the confluent portion 47 of the nozzle 41 is provided on the plane that is continuous with the observation window 38 that is provided on the distal end section body 36. Therefore, the atomized gas/liquid mixture fluid, which is mixed in the confluent portion 47, is jetted from the jet outlet 43 toward the observation window 38, and the contamination adhering to the observation window 38 can efficiently be blown off and cleaned. Moreover, since the gas/liquid mixture fluid is the atomized fluid, no drops of water remain on the surface of the observation window 38, and the field of vision can instantaneously be secured.

Figure 10:
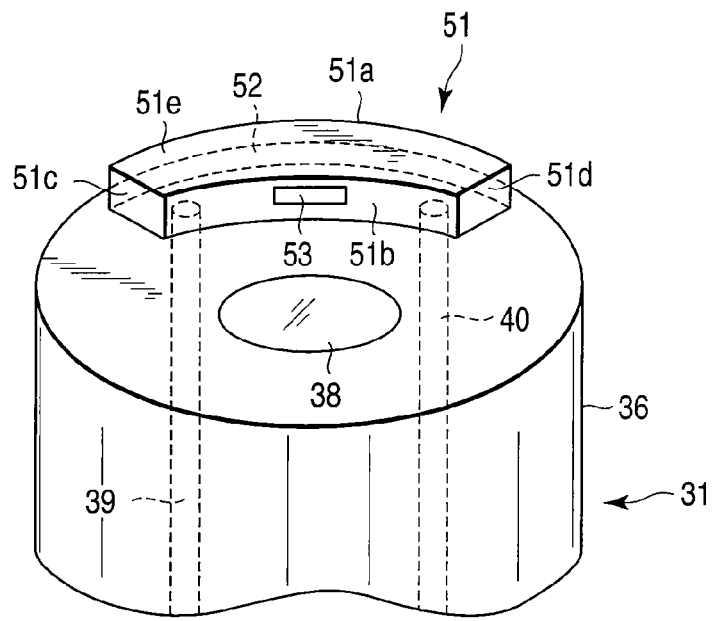
FIG. 10 is a perspective view of a nozzle of a distal end section body according to a third embodiment of the present invention.
Figure 11:
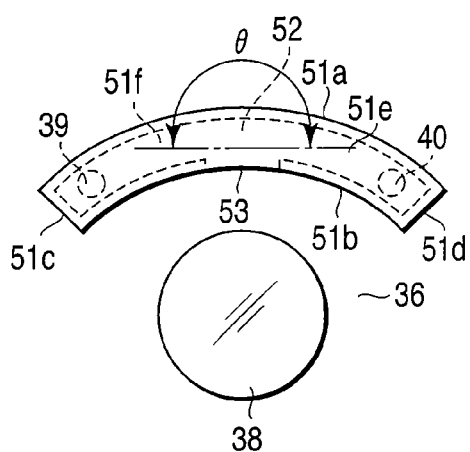
FIG. 11 is a front view of the nozzle of the distal end section body in the third embodiment.

FIG. 10 and FIG. 11 show a third embodiment of the invention. The structural parts common to those in the second embodiment (see FIG. 6 to FIG. 8) are denoted by like reference numerals, and a description thereof is omitted.

An arcuate nozzle 51 is integrally provided at a front end portion of the distal end section body 36 of the endoscope 31 along the outer peripheral part of this front end portion. Specifically, the nozzle 51 includes a space portion 51f which is surrounded by an outer peripheral wall 51a extending along the outer peripheral portion of the distal end section body 36, an inner peripheral wall 51b surrounding a part of the outer periphery of the observation window 38, a left end wall 51c which defines a left side surface of the nozzle 51 in FIG. 10, a right end wall 51d which defines a right side surface of the nozzle 51, and an arcuate front wall 51e. The space portion 51f is curved in an arcuate shape according to the curvature of the outer peripheral wall 51a and inner peripheral wall 51b. The gas feed path 39 is open on the left end wall 51c side in the space portion 51f of the nozzle 51. On the right end wall 51d side, the liquid feed path 40 is open. Accordingly, the gas feed path 39 and the liquid feed path 40 are open to the front end side of the distal end section body 36 of the endoscope 31, and are opposed to the inner surface of the front wall 51e of the nozzle 51.

An intermediate part in the longitudinal direction of the nozzle 51 is provided with a confluent portion 52 which combines and mixes the gas that is supplied from the gas feed path 39 and the liquid that is supplied from the liquid feed path 40. The flow path diameter of the confluent portion 52 is set to be greater than the flow path diameter of each of the gas feed path 39 and liquid feed path 40. Thereby, the gas supplied from the gas feed path 39 and the liquid supplied from the liquid feed path 40 collide in the confluent portion 52 at an obtuse angle, and are made turbulent and efficiently mixed. Further, a jet outlet 53, which is formed of a laterally elongated rectangular hole, is provided in the inner peripheral wall 51b of the nozzle 51, which is opposed to the confluent portion 52. The gas/liquid mixture fluid, which is made confluent and mixed in the confluent portion 52, is jetted from the jet outlet 53 toward the observation window 38.

With the above-described structure, the following advantageous effects can be obtained. Specifically, the confluent portion 52 of the nozzle 51 is provided on the plane that is continuous with the observation window 38 of the distal end section body 36. The gas supplied from the air feed path 39 flows from the opening end of the gas feed path 39 toward the confluent portion 52 within the space portion 51f. The liquid supplied from the liquid feed path 40 flows from the opening end of the liquid feed path 40 toward the confluent portion 52 within the space portion 51f. Thus, the gas supplied from the gas feed path 39 and the liquid supplied from the liquid feed path 40 collide in the confluent portion 52, and are made turbulent and mixed into an atomized gas/liquid mixture fluid. The atomized gas/liquid mixture fluid is jetted from the jet outlet 53 toward the observation window 38. Thereby, the contamination adhering to the observation window 38 can efficiently be blown off and cleaned by the atomized gas/liquid mixture fluid.

FIG. 12A and FIG. 12B show a fourth embodiment of the invention. The structural parts common to those in the second embodiment (see FIG. 6 to FIG. 8) and the third embodiment (see FIG. 10 and FIG. 11) are denoted by like reference numerals, and a description thereof is omitted.

An observation window 38 and an illumination window 37 are provided at a front end portion of the distal end section body 36 of the endoscope 31. As shown in FIG. 12B, a projection portion 36b is provided adjacent to the observation window 38. The projection portion 36b projects forward from a plane 36a in which the observation window 38 is provided. An inclined surface 36c is formed between the plane 36a at the front end of the distal end section body 36 and the projection portion 36b. The projection portion 36b is provided with a nozzle 51 which is integral with the distal end section body 36. The nozzle 51 has basically the same structure as in the third embodiment. The nozzle 51 is curved in an arcuate shape according to the curvature of the distal end section body 36. Further, a confluent portion 52 is provided at an intermediate part of the nozzle 51. The nozzle 51 is provided with a jet outlet 58 at a position corresponding to the confluent portion 52. The jet outlet 58 is parallel to the inclined surface 36c and has a fluid guide surface 58a which projects toward the observation window 38.

In addition, a gas feed path 39 is open on the left end side (in FIG. 12A) in the space portion of the nozzle 51, and a liquid feed path 40 is open on the right end side. The gas feed path 39 and liquid feed path 40 are open toward the front end side of the distal end section body 36 of the endoscope 31, and are opposed to the inner surface of the nozzle 51.

The flow of the gas supplied from the gas feed path 39 and the flow of the liquid supplied from the liquid feed path 40 collide in the confluent portion 52, and are made turbulent and mixed into an atomized gas/liquid mixture fluid. In this case, the angle θ, which is formed between the direction of the flow of the gas, which is supplied from the gas feed paths 39, and the direction of the flow of the liquid, which is supplied from the liquid feed paths 40, is set at an obtuse angle. Thus, the angle θ is set at such an angle that the gas and the liquid are easily mixed and made turbulent.

With the above-described structure, the following advantageous effects can be obtained. Specifically, the confluent portion 52 of the nozzle 51 and the jet outlet 58 are parallel to the observation window 38 of the distal end section body 36, and are provided in a manner to project forward from the observation window 38. The angle θ, which is formed between the direction of the flow of the gas, which is supplied from the gas feed paths 39, and the direction of the flow of the liquid, which is supplied from the liquid feed paths 40, is set at an obtuse angle. Thereby, the flow of the gas, which is supplied from the gas feed paths 39, and the flow of the liquid, which is supplied from the liquid feed paths 40, collide in the confluent portion 52 and are mixed into a gas/liquid mixture fluid. Then, the gas/liquid mixture fluid collides with the inner surface of the nozzle 51 and is further mixed in an atomized state. The atomized gas/liquid mixture fluid is jetted from the jet outlet 58 toward the observation window 38. Thereby, the contamination adhering to the observation window 38 can be blown off and cleaned.

FIG. 13A and FIG. 13B show a fifth embodiment of the invention. The structural parts common to those in the second embodiment (see FIG. 6 to FIG. 8) are denoted by like reference numerals, and a description thereof is omitted. As shown in FIG. 13A, a front end portion of the distal end section body 36 of the endoscope 31 includes an arcuate nozzle 59 which is curved in an arcuate shape along the outer peripheral part of the distal end section body 36. The nozzle 59 has the same structure as the nozzle 41 of the second embodiment. As shown in FIG. 13B, the nozzle 59 includes a space portion 59c which is surrounded by walls. In FIG. 13A, an L-shaped conduit 60a, which is connected to the gas feed path 39, penetrates a lower side end wall 59a of the nozzle 59 and is open to the inside of the nozzle 59. In addition, in FIG. 13A, an L-shaped conduit 60b, which is connected to the liquid feed path 40, penetrates an upper side end wall 59b of the nozzle 59 and is open to the inside of the nozzle 59.

Accordingly, the opening portions of the gas feed path 39 and the liquid feed path 40 are opposed to a confluent portion 61 at an intermediate part of the nozzle 59. Further, a jet outlet 63, which is directed to the observation window 38, is provided in the inner peripheral wall of the nozzle 59, which is opposed to the confluent portion 61. The jet outlet 63 is configured to jet the gas/liquid mixture fluid, which is made confluent and mixed in the confluent portion 61, toward the observation window 38. Further, the angle θ, which is formed between the direction of the flow of the gas, which is supplied from the gas feed paths 39, and the direction of the flow of the liquid, which is supplied from the liquid feed paths 40, is set at an obtuse angle. Thus, the angle θ is set at such an angle that the gas and the liquid are easily mixed and made turbulent.

With the above-described structure, the following advantageous effects can be obtained. Specifically, the confluent portion 61 of the nozzle 59 is provided on the plane that is continuous with the observation window 38 of the distal end section body 36. The gas supplied from the air feed path 39 and the liquid supplied from the liquid feed path 40 are mixed in the confluent portion 61 into an atomized gas/liquid mixture fluid. The atomized gas/liquid mixture fluid is jetted from the jet outlet 63 toward the observation window 38. Thereby, the contamination adhering to the observation window 38 can be blown off and cleaned.

FIG. 14A and FIG. 14B show a sixth embodiment of the invention. The structural parts common to those in the fifth embodiment (see FIG. 13A and FIG. 13B) are denoted by like reference numerals, and a description thereof is omitted. A front end portion of the distal end section body 36 of the endoscope 31 includes an arcuate nozzle 59 which is curved in an arcuate shape along the outer peripheral part of the distal end section body 36. The arcuate nozzle 59 has the same structure as the nozzle 41 of the second embodiment. As shown in FIG. 14B, the nozzle 59 includes a space portion 59c which is surrounded by walls. In FIG. 14A, a U-shaped conduit 64a, which is connected to the gas feed path 39, penetrates a front surface portion of the nozzle 59 on a lower end wall 59a side of the nozzle 59 and is open to the inside of the nozzle 59. In addition, in FIG. 14A, a U-shaped conduit 64b, which is connected to the liquid feed path 40, penetrates a front surface portion of the nozzle 59 on an upper end wall 59b side of the nozzle 59 and is open to the inside of the nozzle 59.

Accordingly, the opening portions of the gas feed path 39 and the liquid feed path 40 are opposed to the distal end face of the distal end section body 36. Further, a confluent portion 65 is provided at an intermediate part of the nozzle 59. A jet outlet 66 is provided in the inner peripheral wall of the nozzle 59, which is opposed to the confluent portion 65. The jet outlet 66 is configured to jet the gas/liquid mixture fluid, which is made confluent and mixed in the confluent portion 65, toward the observation window 38. Further, the angle θ, which is formed between the direction of the flow of the gas, which is supplied from the gas feed paths 39, and the direction of the flow of the liquid, which is supplied from the liquid feed paths 40, is set at an obtuse angle. Thus, the angle θ is set at such an angle that the gas and the liquid are easily mixed and made turbulent.

With the above-described structure, the following advantageous effects can be obtained. Specifically, the confluent portion 65 of the nozzle 59 is provided on the plane that is continuous with the observation window 38 of the distal end section body 36. The gas supplied from the air feed path 39 and the liquid supplied from the liquid feed path 40 are mixed in the confluent portion 65 into an atomized gas/liquid mixture fluid. The atomized gas/liquid mixture fluid is jetted from the jet outlet 66 toward the observation window 38. Thereby, the contamination adhering to the observation window 38 can be blown off and cleaned.

In the second to seventh embodiments, the flexible endoscopes have been described. Needless to say, the invention is also applicable to rigid endoscopes.

FIG. 15 to FIG. 18 show a seventh embodiment of the invention. The structural parts common to those in the second embodiment (see FIG. 6 to FIG. 8) are denoted by like reference numerals, and a description thereof is omitted. The present embodiment shows a distal end cap-equipped endoscope. An observation window 38 and an illumination window 37 are provided on a distal end section body 72 of an insertion section 71 of a flexible endoscope 70. In addition, a gas feed path 39 and a liquid feed path 40 are provided in the insertion section 71. Openings of the gas feed path 39 and liquid feed path 40 are provided on a front end face of the distal end section body 72.

As shown in FIG. 16, an annular engagement groove 73 is provided on an outer peripheral surface of the distal end section body 72. A distal end cap 75 having a circular cylindrical shape is detachably attached to the distal end section body 72. An engagement projection 74, which is engaged with the engagement groove 73, is provided on an inner peripheral surface of a rear end portion of the distal end cap 75.

In the front end portion of the distal end cap 75, an arcuate nozzle 76 is integrally provided along the outer peripheral portion of the distal end cap 75. Specifically, as shown in FIG. 17, the nozzle 76 includes a space portion 76f which is surrounded by an outer peripheral wall 76a extending along the outer peripheral portion of the distal end cap 75, an inner peripheral wall 76b surrounding a part of the outer periphery of the observation window 38, a left end wall 76c which defines a left side surface of the nozzle 76 in FIG. 17, a right end wall 76d which defines a right side surface of the nozzle 76, and an arcuate front wall 76e (see FIG. 16). The space portion 76f is curved in an arcuate shape according to the curvature of the outer peripheral wall 76a and inner peripheral wall 76b. Further, the gas feed path 39 is open on the left end wall 76c side in the space portion 76f of the nozzle 76. On the right end wall 76d side, the liquid feed path 40 is open. Accordingly, the gas feed path 39 and the liquid feed path 40 are open to the front end side of the distal end cap 75, and are opposed to the inner surface of the front wall 76e of the nozzle 76.

An intermediate part in the longitudinal direction of the nozzle 76 is provided with a confluent portion 77 which combines and mixes the gas that is supplied from the gas feed path 39 and the liquid that is supplied from the liquid feed path 40. Further, a jet outlet 78 is provided in the inner peripheral wall 76b of the nozzle 76, which is opposed to the confluent portion 77. The jet outlet 78 is configured to jet the gas/liquid mixture fluid, which is made confluent and mixed in the confluent portion 77, toward the observation window 38. Further, the angle θ, which is formed between the direction of the flow of the gas, which is supplied from the gas feed paths 39, and the direction of the flow of the liquid, which is supplied from the liquid feed paths 40, is set at an obtuse angle. Thus, the angle θ is set at such an angle that the gas and the liquid are easily mixed and made turbulent.

With the above-described structure, the following advantageous effects can be obtained. Specifically, the confluent portion 77 of the nozzle 76 is provided on the plane that is continuous with the observation window 38 of the distal end section body 72. The gas supplied from the air feed path 39 and the liquid supplied from the liquid feed path 40 are mixed in the confluent portion 77 into an atomized gas/liquid mixture fluid. The atomized gas/liquid mixture fluid is jetted from the jet outlet 78 toward the observation window 38. Thereby, the contamination adhering to the observation window 38 can be blown off and cleaned.

The present invention is not limited directly to the above-described embodiments. In practice, the structural elements can be modified and embodied without departing from the spirit of the invention. Various inventions can be made by properly combining the structural elements disclosed in the embodiments. For example, some structural elements may be omitted from all the structural elements disclosed in the embodiments. Furthermore, structural elements in different embodiments may properly be combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion section which is inserted in a body cavity;
   a distal end section body which constitutes a distal end section of the insertion section and has at least an observation window at a distal end surface;
   a liquid feed path which communicates with a liquid feed source to supply liquid and has a plurality of opening ends open to the outer peripheral side of the distal end surface at intervals;
   a gas feed path which communicates with a gas feed source to supply gas and has a plurality of opening ends open on the distal end surface opposite to the opening ends of the liquid feed path across the observation window; and
   a nozzle which forms an M-shaped path formed of a first V-shaped path extending from an opening end of the liquid feed path along an outer peripheral portion and bending toward the center of the distal end section, a second V-shaped path extending from an opening end of the gas feed path along the outer peripheral portion and bending toward the center of the distal end section, and a confluent portion at which an extended end of the first path and an extended end of the second path are connected with each other at an obtuse angle more than 90° and the gas and the fluid from each of the opening ends collide and mix with each other to be a gas/liquid mixture fluid, the nozzle comprising a jet outlet to let the gas/liquid mixture fluid toward the observation window.

2. The endoscope according to claim 1, wherein the confluent portion is provided on a plane which is continuous with the observation window of the distal end section body.

3. The endoscope according to claim 1, wherein the confluent portion is provided on a distal end side further than the observation window of the distal end section body.

4. The endoscope according to claim 1, wherein the confluent portion is formed in a part of a conduit which is curved along an outer peripheral portion of the distal end section body.

5. The endoscope according to claim 1, wherein the gas from the gas feed path and the liquid from the liquid feed path collide at the obtuse angle in the confluent portion.

6. The endoscope according to claim 1, wherein the nozzle has two conduits extending from an outer peripheral portion of the distal end section body toward a central portion of the distal end section body,
   one of the two conduits has a communication portion which communicates with the liquid feed path on the outer peripheral portion side of the distal end section body,
   the other of the two conduits has a communication portion which communicates with the gas feed path on the outer peripheral portion side of the distal end section body, and
   the confluent portion and the jet outlet are provided at the central portion of the distal end section body.

7. The endoscope according to claim 1, further comprising: a distal end cap which is detachably attached to the distal end section body.

8. The endoscope according to claim 7, wherein the confluent portion is formed in a part of a conduit which is curved along an outer peripheral portion of the distal end cap.

9. The endoscope according to claim 7, wherein the gas from the gas feed path and the liquid from the liquid feed path collide at the obtuse angle in the confluent portion.

10. The endoscope according to claim 7, wherein the confluent portion is provided on a plane which is continuous with the observation window of the distal end section body.

11. The endoscope according to claim 1, further comprising:
    a cleaning sheath body which is fitted over an insertion section of an endoscope having at least an observation window at a distal end section body.

12. The endoscope according to claim 11, wherein the cleaning sheath body is a multi-lumen tube, and the liquid feed path and the gas feed path are provided along an axial direction of the tube.

13. The endoscope according to claim 11, wherein the confluent portion is formed in a part of a conduit which is curved along an outer peripheral portion of the distal end section body of the endoscope.

14. The endoscope according to claim 11, wherein the gas from the gas feed path and the liquid from the liquid feed path collide at the obtuse angle in the confluent portion.

15. The endoscope according to claim 11, wherein the confluent portion is provided on a plane which is continuous with the observation window of the distal end section body.

* * * * *